United States Patent [19]

Nickerson, Jr.

[11] Patent Number: 5,287,727
[45] Date of Patent: Feb. 22, 1994

[54] FIXTURE FOR PRESSURE TESTING SIGHT GLASSES

[75] Inventor: Earl S. Nickerson, Jr., Little Compton, R.I.

[73] Assignee: The United States of America as represented by the Secretary of the Navy, Washington, D.C.

[21] Appl. No.: 901,286

[22] Filed: Jun. 19, 1992

[51] Int. Cl.⁵ .............................................. G01M 3/02
[52] U.S. Cl. .......................................... 73/37; 73/49.8
[58] Field of Search ....................... 73/37, 40, 49.8, 46

[56] References Cited

U.S. PATENT DOCUMENTS 2,345,387  3/1944  Elsey ........................................ 73/40
2,855,777  10/1958 Garrett ...................................... 73/40

FOREIGN PATENT DOCUMENTS 1307263  4/1987  U.S.S.R. .................................. 73/40

Primary Examiner—Hezron E. Williams
Assistant Examiner—Joseph W. Roskos
Attorney, Agent, or Firm—Michael J. McGowan; Prithvi C. Lall; Michael F. Oglo

[57] ABSTRACT

A fixture for pressure testing sight glasses includes a base having a recessed pressure chamber therein, a peripheral seal ring in the pressure chamber and a supply passage for supplying a pressurized fluid to the pressure chamber. The test fixture is operable by securing a sight glass on the fixture so that the sight glass is received in sealing engagement with the seal ring above the pressure chamber in order to apply a predetermined fluid pressure to the sight glass.

9 Claims, 2 Drawing Sheets

FIXTURE FOR PRESSURE TESTING SIGHT GLASSES

STATEMENT OF GOVERNMENT INTEREST

The invention described herein may be manufactured and used by or for the Government of The United States of America for governmental purposes without the payment of any royalties thereon or therefor.

BACKGROUND OF THE INVENTION (1) Field of the Invention

The instant invention relates to quality testing apparatus, and more particularly to an improved test fixture for pressure testing a sight glass prior to use.

(2) Description of the Prior Art

Sight glasses are frequently used to detect the presence of liquids, and/or to observe liquid levels in various high pressure vessels and other areas which are exposed to high pressures. In this connection, when sight glasses are used in such applications they are generally assembled in sealing engagement in permanent mounting assemblies in order to secure them in position over apertures or other openings in vessels. However, it has been found that it can often be important to pressure test sight glasses designed for certain critical high pressure applications prior to use to be certain that they can withstand sufficiently high fluid pressures. The heretofore known test procedures for testing sight glasses have generally included the steps of mounting the sight glasses in test mounting assemblies which resemble the mounting assemblies utilized for permanently mounting sight glasses for actual use and then exposing the sight glasses to relatively high levels of fluid pressure. However, it has been found that sight glasses frequently become damaged while assembling them in, or disassembling them from test mounting assemblies, and that substantial amounts of labor are often required to assemble sight glasses in and disassemble them from test mounting assemblies.

While various types of test fixtures have been heretofore available for pressure testing various specific articles prior to use, they have generally not been adaptable for use in testing sight glasses, and hence, the previously available test fixtures are believed to be of only general interest with respect to the subject invention. In this connection, test fixtures representing the closest prior art to the subject invention of which the applicant is aware are disclosed in the U.S. Pat. Nos. to Schlein No. 2,993,368; Quackenbush No. 3,196,665; and Forman No. 3,559,459. However, these references fail to disclose or suggest a test fixture which can be utilized for testing a sight glass prior to use.

SUMMARY OF THE INVENTION

The instant invention provides an effective test fixture for testing a sight glass prior to use. Specifically, the instant invention comprises a base member having a substantially planar receiving surface thereon, a recessed pressure chamber in the receiving surface, and a supply passage which is connectable to a supply of pressurized fluid for supplying the fluid to the pressure chamber. The peripheral configuration of the pressure chamber is preferably approximately the same as that of a sight glass to be tested, and the dimension of the pressure chamber is at least slightly smaller than the peripheral dimension of the sight glass. The test fixture further includes a resilient seal ring which is received in the pressure chamber so that it extends along the perimeter thereof and projects at least slightly above the receiving surface. The test fixture preferably still further includes a plurality of positioning pins on the receiving surface for positioning the sight glass on the fixture so that it is positioned over the pressure chamber.

The test fixture is operable by assembling a sight glass on the seal ring so that it is positioned over the pressure chamber with the outer perimeter of the sight glass located in slightly outwardly spaced relation around the perimeter of the pressure chamber. The sight glass is then removably secured on the test fixture utilizing hydraulic press, and the supply passage is connected to a supply of pressurized fluid for supplying pressurized fluid to the pressure chamber. The supply of pressurized fluid is then actuated so that a sufficient level of pressure is applied to the sight glass to insure that it can be effectively utilized in its intended application. Once the sight glass has been adequately tested in this manner, the pressure in the pressure chamber is released and the hydraulic press is deactuated so that the sight glass can be removed from the fixture.

It has been found that the test fixture of the instant invention can be effectively utilized for testing sight glasses. Specifically, it has been found that sight glasses can be quickly and easily assembled on the test fixture and that they can also be quickly and easily disassembled from the test fixture after testing. It has been further found that the specific construction of the test fixture makes it simple and easy for a user to assemble sight glasses with the fixture and to disassemble them therefrom, without causing damage to the sight glasses.

BRIEF DESCRIPTION OF THE DRAWINGS

A more complete understanding of the invention and many of the attendant advantages thereto will be readily appreciated as the same becomes better understood by reference to the following detailed description when considered in conjunction with the accompanying drawing wherein.

DESCRIPTION OF THE PREFERRED EMBODIMENTS

Figure 1:
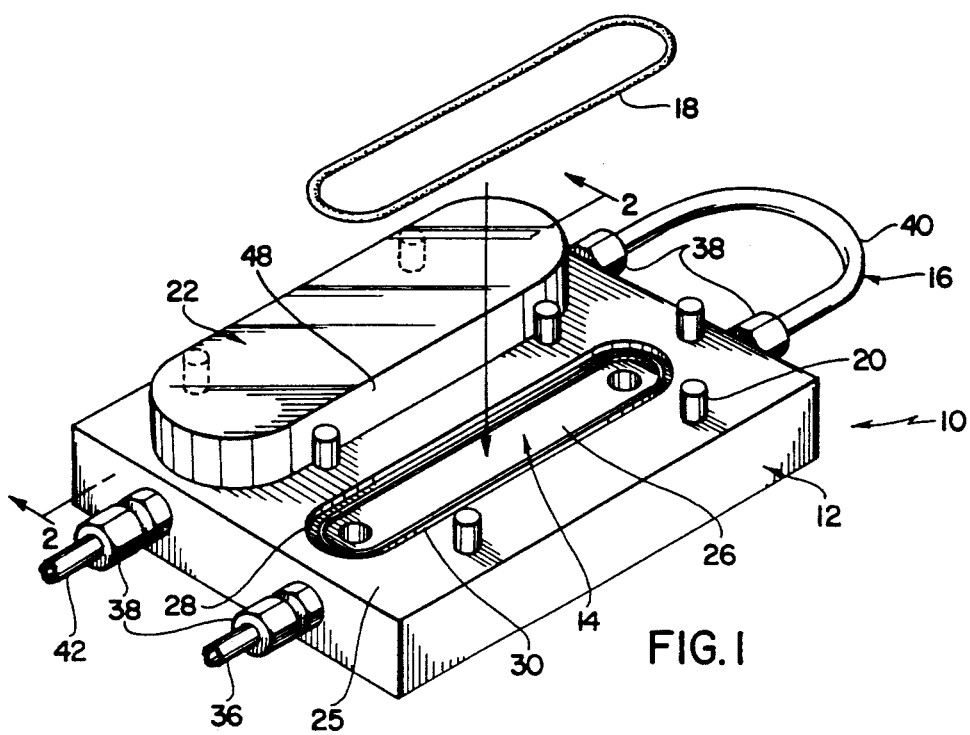
FIG. 1 is a partially exploded perspective view of a first embodiment of test fixture of the instant invention with a sight glass thereon.
Figure 2:
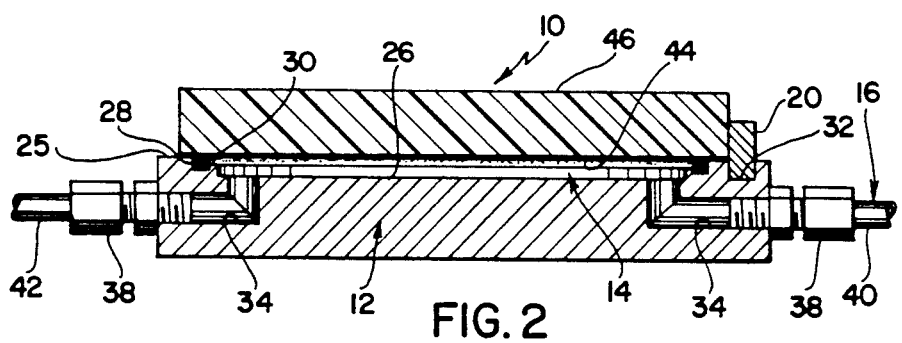
FIG. 2 is a sectional view taken along the line 2—2 in FIG. 1.
Figure 3:
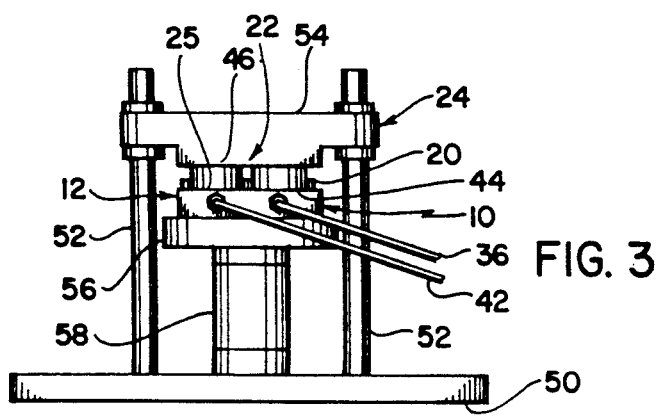
FIG. 3 is a front elevational view of a test assembly comprising the test fixture and a pair of sight glasses assembled in a press.

Referring now to the drawings, a first embodiment of the test fixture of the instant invention is illustrated and generally indicated at 10 in FIGS. 1 through 3. The test fixture 10 comprises a base member generally indicated at 12 having a pair of pressure chambers generally indicated at 14 therein, a pressurized fluid supply assembly generally indicated at 16 for supplying pressurized fluid to each of the pressure chambers 14, a seal ring 18 in each of the pressure chambers 14, and a plurality of alignment pins 20 on the base 12. The test fixture 10 is adapted for use in testing a pair of sight glasses 22 by exposing the sight glasses 22 to a predetermined level of pressure in order to determine whether or not the sight glasses 22 can be effectively utilized in certain high pressure applications. Specifically, the test fixture 10 is adapted to utilized for testing the sight glasses 22 by first securing the sight glasses 22 on the fixture 10 utilizing a hydraulic press generally indicated at 24, and by then supplying a pressurized fluid to the test fixture 10 through the supply assembly 16 in order to expose the sight glasses 22 to a predetermined level of pressure.

The base 12, as herein embodied, is constructed from a solid block of aluminum, although it will be understood that Various other materials of sufficient strength can also be effectively utilized for the base 12. The base 12 as herein embodied has a substantially flat, planar, upper receiving surface 25 thereon, and it has a pair of recessed pressure chambers 14 formed therein. The pressure chambers 14 are of elongated oval shaped configuration, and each includes an enlarged central area 26 and a peripheral 0-ring channel 28 which is separated from the respective central area 26 thereof by a shoulder 30 which is recessed slightly below the surface 25. The base 12 has a plurality of relatively shallow bores 32 formed therein which extend downwardly from the receiving surface 25 around the peripheries of the pressure chambers 14 for aligning sight glasses 22 with the pressure chambers 14 on the surface 25. Also formed in the base 12 are four fluid passages 34 which extend inwardly through the base 12 to the pressure chambers 14. The outer end portions of the passages 34 are formed as threaded sockets, and as illustrated, one of the passages 34 is provided extending outwardly from each end of each of the pressure chambers 14 to the exterior of the base 12.

The pressurized fluid supply assembly 16 comprises an inlet tube 36 which is connected to the base 12 with a coupling assembly 38 so that it communicates with one of the passages 34. The pressurized fluid supply assembly 16 further comprises a connecting tube 40 which is connected between the passages 34 extending outwardly from the pressure chambers 14 at one end of the base 12 with a pair of coupling assemblies 38, and an outlet tube 42 which is connected to the remaining passage 34 with a coupling assembly 38. Accordingly, pressurized fluid can be supplied to the pressure chambers 14 so that it passes inwardly through the inlet tube 36 into one pressure chamber 14, and then outwardly through the connecting tube 40 into the other pressure chamber 14.

The seal rings 18 comprise conventional 0-rings, and they are dimensioned to be received in the 0-ring channels 28 in the pressure chambers 14 so that they are positioned adjacent the outer perimeters of the respective pressure chambers 14 thereof. The seal rings 18 and the 0-ring channels 28 are dimensioned and configured so that the seal rings 18 normally project upwardly slightly above the receiving surface 25 when the seal rings 18 are in relaxed or uncompressed dispositions.

The alignment pins 20, as herein embodied, comprise relatively short metal plugs which are received and secured in the bores 32 so that they extend upwardly from the receiving surface 25 around the pressure chambers 14. Accordingly, the alignment pins 20 are effectively operative for aligning sight glasses 22 with the pressure chambers 14 during use of the fixture 10. Alignment pins are also used to protect the sight glass from being broken by direct pressure from the (2) metal surfaces of the bottom and the top plate.

The sight glasses 22 are of conventional construction, and they are made of a suitable material, such as a suitable glass. Each of the sight glasses 22 has opposite first and second faces 44 and 46, and a perimeter surface 48 which extends between the faces 44 and 46. The sight glasses 22, and the pressure chambers 14 are dimensioned so that when the sight glasses 22 are positioned on the seal rings 18 above the receiving surface 25 between the alignment pins 20, the perimeters of the sight glasses 22 as defined by the perimeter surfaces 48 thereof, are spaced outwardly around the outer perimeters of the respective pressure chambers 14 thereof. In other words, the pressure chambers 14 are of at least slightly smaller dimension than the sight glasses 22 so that the seal rings 18 are receivable in effective sealing engagement with the first faces 44 of the sight glasses 22 when the sight glasses 22 are assembled on the fixture 10, so that the first faces 44 thereof face their respective pressure chambers 14.

The press 24 is of conventional construction and it comprises a mounting brace 50 having a plurality of upstanding posts 52 thereon, and an upper frame 54 which is secured on the posts 52 in upwardly spaced relation to the base 50. The press 24 further includes a movable plate 56 which is supported on a hydraulic piston 58. The press 24 is actuatable by applying hydraulic pressure to the piston 58 in order to move the movable plate 56 upwardly toward the upper frame 54. Accordingly, when the fixture 10 is assembled on the plate 56 with a pair of the sight glasses 22 received on the fixture 10 so that the first faces 44 thereof face downwardly, the press 24 is actuatable for moving the fixture 10 upwardly so that the second faces 46 of the sight glasses 22 are moved into engagement with the upper frame 54. The press 24 is preferably operative in this manner for applying hydraulic pressures of at least approximately 10,000 lbs. between the plate 56 and the stationary frame 54 in order to effectively retain the sight glasses 22 on the fixture 10 during a testing operation.

Figure 4:
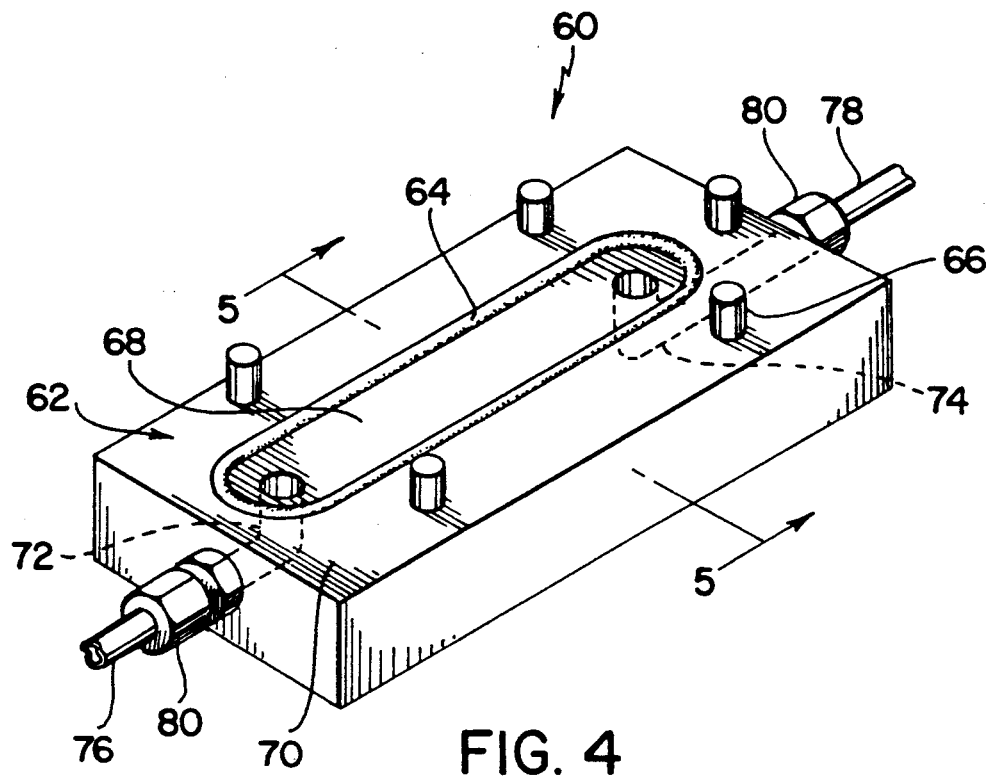
FIG. 4 is a perspective view of a second embodiment of the test fixture.
Figure 5:
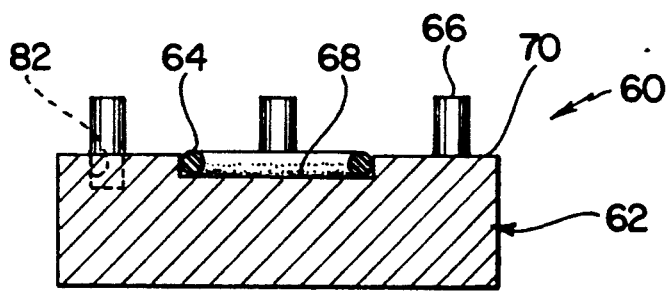
FIG. 5 is a sectional view taken along line 5—5 in FIG. 4.

For use and operation of the test fixture 10, a pair of the sight glasses 22 are assembled on the receiving surface 25 so that the first faces 44 of the sight glasses 22 are supported on the seal rings 18 and positioned in aligned relation with their respective pressure chambers 14. Further, the fixture 10 and the sight glasses 22 are assembled in the press 24 so that the fixture 10 is received on the plate 56. The supply line 36 is connected through suitable valving to a supply of pressurized fluid, and the outlet line 42 is connected through suitable valving to a return fluid reservoir. Thereafter, the press 24 is actuated to apply pressure to the sight glasses 22 in order to effectively retain the sight glasses 22 on the fixture 10, and a pressurized fluid is supplied to the fixture 10 through the supply tube 36. In this connection, as fluid is initially applied to the fixture 10 through the supply tube 36, the fluid is allowed to pass through the fixture 10 to bleed air from the supply tube 36, the connecting tube 40, the return tube 42, the passages 34, and the pressure chambers 14. Thereafter, the return tube 42 is closed, and a predetermined level of fluid pressure is applied to the fixture 10 through the supply line 36. Accordingly, the sight glasses 22 are exposed to a predetermined level of fluid pressure in order to test the sight glasses 22 prior to actual use. Once the sight glasses 22 have been tested in this manner the return line 42 is opened and the supply of pressurized fluid 36 is discontinued. The hydraulic press 24 is then operated to lower the plate 56 so that the sight glasses 22 can be removed from the fixture 10. In this connection, because the sight glasses 22 are merely positioned on the seal rings 18, there is little chance for damaging the sight glasses 22 as they are assembled onto, and disassembled from, the fixture 10. Hence, the sight glasses 22 can be effectively tested without significant risk of causing damage thereto. Further, because of the simple and effective manner in which the sight glasses 22 can be assembled onto and disassembled from the fixture 10, the sight glasses 22 can be tested in a relatively short period of time. Referring now to FIGS. 4 and 5, a second embodiment of the test fixture of the instant invention is illustrated and generally indicated at 60. The test fixture 60 comprises a base generally indicated at 62, a seal ring 64, and a plurality of alignment pins 66.

The base 62 is preferably made from a suitable durable material, such as aluminum, and it has a pressure chamber 68 formed therein. The pressure chamber 68 is generally similar to the pressure chamber 14, although it does not include an 0-ring channel 28. The base further includes a receiving surface 70 and it has inlet and outlet passages 72 and 74 formed therein which are connectable to inlet and outlet fluid lines 76 and 78, respectively, with coupling assemblies 80 for carrying pressurized fluid to and from the fixture 60.

The seal ring 64 comprises a conventional 0-ring, and it is preferably made from a suitable elastomeric material, such as a rubber. The seal ring 64 is received in the pressure chamber 68 so that it is positioned adjacent to the perimeter of the pressure chamber 68. Further, the seal ring 64 is formed so that it projects upwardly slightly above the receiving surface 70 when the seal ring 64 is in a normal, uncompressed disposition.

The alignment pins 66 are received in the shallow bores 82 in the base 62 so that they are positioned around the pressure chamber 68. In this connection, the fixture 60 is dimensioned for use in testing a sight glass 22 having an at least slightly larger peripheral dimension than the perimeter of the pressure chamber 68 so that the seal ring 64 can be effectively utilized for sealing against the bottom face of the sight glass 22 in the manner hereinabove set forth in connection with the test fixture 10.

The test fixture 60 is adapted to be utilized in a manner similar to that hereinabove described with respect to the test fixture 10. Specifically, once a sight glass 22 has been assembled on the fixture 60, the fixture 60 and the sight glass 22 can be clamped in a press, such as the press 24, for retaining the sight glass 22 on the fixture 60. Thereafter, a pressurized fluid can be supplied to the test fixture 60 through the supply line 76, and air can be bled from the fixture 60 through the return line 78. Thereafter, the return line 78 can be shut off to apply a predetermined level of pressure to the sight glass 22 with pressurized fluid supplied through the supply line 76.

It is seen therefore that the instant invention provides an effective fixture for testing sight glasses. The fixtures 10 and 60 can be readily assembled in presses, such as the press 24, and sight glasses, such as the sight glass 22, can be effectively assembled thereon for exposing the sight glasses 22 to predetermined levels of pressure. Once the sight glasses 22 have been exposed to the desired levels of pressure, the pressures can be readily released and the sight glasses can be quickly and easily removed from the fixtures 10 or 60 without risking damage to the sight glasses 22. Hence, it is seen that the instant invention represents a significant advancement in the art relating to test apparatus which has substantial commercial merit.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A test fixture for pressure testing a sight glass, said sight glass having opposite first and second faces and a perimeter surface extending between said first and second faces defining a perimeter of said sight glass, said first face being substantially flat, said test fixture comprising a base member having a receiving surface thereon and having a recessed pressure chamber therein opening outwardly through said receiving surface, said base member also having a supply passage therein which is connectable to a supply of pressurized fluid for supplying said fluid to said pressure chamber, said pressure chamber being defined by an inner pressure chamber surface and having a perimeter, the dimension of said pressure chamber as defined by the perimeter thereof being at least slightly smaller than the dimension of said sight glass as defined by the perimeter of said sight glass, and resiliently expandable seal ring means in said pressure chamber adjacent the perimeter thereof an extending slightly above the plane of said receiving surface, said test fixture being operable by securing said sight glass thereon over said pressure chamber so that the perimeter of said sight glass is spaced outwardly around the perimeter of said pressure chamber and supplying a pressurized fluid to said pressure chamber through said supply passage so that said seal ring means is urged into sealing engagement with both said sight glass and said pressure chamber surface in order to apply to said sight glass with said pressurized fluid.

2. The test fixture of claim 1, further comprising alignment means for aligning said sight glass on said receiving surface so that the perimeter of said sight is spaced outwardly around the perimeter of said pressure chamber.

3. In the test fixture of claim 2, said alignment means comprising a plurality of pins spaced outwardly from said pressure chamber on said receiving surface.

4. In the test fixture of claim 1, said seal ring means comprising an 0-ring having an outer perimeter of substantially the same length as the perimeter of said pressure chamber.

5. In the test fixture of claim 1, said pressure chamber comprising a recessed central portion, a recessed peripheral seal channel extending around said central portion, and a shoulder between said central portion and said seal channel, said seal ring means being disposed in said seal channel.

6. In the test fixture of claim 5, said seal ring means comprising an 0-ring.

7. In the test fixture of claim 1, said seal ring means extending upwardly slightly beyond the plane of said receiving surface.

8. A method for pressure testing a sight glass, said sight glass having opposite first and second faces and a perimeter surface extending between said first and second faces, said first face being substantially flat, said method comprising the steps of:

securing said sight glass on a test fixture, said test fixture comprising a base member having a receiving surface thereon and having a recessed pressure chamber therein opening outwardly through said receiving surface, said base member also having a supply passage therein for supplying a pressurized fluid to said pressure chamber, said pressure chamber being defined by an inner pressure chamber surface and having a perimeter, the dimension of said pressure chamber as defined by the perimeter thereof being at least slightly smaller than the dimension of said sight glass as defined by the perimeter of said sight glass, and a resiliently expandable seal ring in said pressure chamber adjacent the perimeter thereof and extending at least to the plane of said receiving surface, said sight glass being secured on said receiving surface so that the perimeter of said sight glass is spaced outwardly around the perimeter of said pressure chamber wherein said step of securing said sight glass comprising positioning said sight glass on said seal ring so that the perimeter of said sight glass is spaced outwardly around the perimeter of said pressure chamber, assembling said test fixture and said sight glass in a clamp and clamping said sight glass on said test fixture; and supplying a pressurized fluid to said pressure chamber through said supply passage so that said seal ring is urged into sealing engagement with both said sight glass and said pressure chamber surface in order to apply pressure to said sight glass with said pressurized fluid.

9. In the method of claim 8, wherein said clamp comprising a press.

* * * * *